United States Patent [19]

Abdulla

[11] Patent Number: 5,445,600
[45] Date of Patent: Aug. 29, 1995

[54] FLOW CONTROL SYSTEMIC TO PULMONARY ARTERIAL SHUNT

[76] Inventor: Ra-id Abdulla, 1507 W. Harrison, Chicago, Ill. 60607

[21] Appl. No.: 235,440

[22] Filed: Apr. 29, 1994

[51] Int. Cl.[6] .............................................. A61M 5/00
[52] U.S. Cl. ..................................................... 604/9
[58] Field of Search ...................... 604/8, 9; 137/68.1; 138/45, 46; 239/533.13

[56] References Cited

U.S. PATENT DOCUMENTS

| | | | |
|---|---|---|---|
| 3,828,764 | 8/1974 | Jones | 604/9 |
| 4,500,487 | 2/1985 | Christie et al. | 138/26 |
| 4,655,771 | 4/1987 | Wallsten | 623/1 |
| 4,733,665 | 3/1988 | Palmaz | 623/1 |
| 4,923,470 | 5/1990 | Dumican | 623/1 |
| 5,007,926 | 4/1991 | Derbyshire | 623/1 |
| 5,019,090 | 5/1991 | Pinchuk | 606/194 |
| 5,061,275 | 10/1991 | Wallsten et al. | 623/1 |
| 5,123,917 | 6/1992 | Lee | 623/1 |
| 5,226,913 | 7/1993 | Pinchuk | 623/1 |

OTHER PUBLICATIONS

Experience with Polytetrafluoroethylene Grafts in Children and Cyanotic Congenital Heart Disease, Opie et al. M. D. Ann. Thoracic Surg 41: 164–168, Feb., 1986.
Boyce, B: Physical Characteristics of Expanded Polytetraflouroylene Grafts, Chapter 33, Biologic and synthetic vascular prostheses Grune & Stratton Inc., 1982.
Woolf, P. K., et al.: A Comparison of Blalock-Taussig, Waterston and Polytetraflouroethylene shunts, The Annals of Thoracic Surgery 38(1), 1984.
Karpawich, P. P., et al.: Modified Blalock-Taussig shunts in infants and young children. The Journal of Thoracic and Cardiovascular Surgery 89(2): 275–279.
Opie, J. C., et al: Experience with Polytetraflouroethylene Grafts in Children with Cyanotic Congenital Heart Disease. The Annals of Thoracic Surgery 42(2): 64–168, 1986.
Ulom, R. L. et al.: The Blalock-Taussig Shunt in Infants: Standard versus modified.
The Annals of Thoracic Surgery 44(5): 539–543, 1987.
McKay, R., et al.: Postoperative Angiographic Assessment of Modified Blalock-Taussig Shunts using expanded Polytetraflouroethylene (Gore-Tex). The Annals of Thoracic Surgery 30(2): 137–145, 1980.
Parsons, J. M., et al.: Balloon Dilatation of Stenosed modified (Polytetraflouoroethylene).
Blalock-Taussig Shunts. Br Heart J 63:228–9, 1989.
Holman, W. L. et al. The Blalock-Taussig shunt: An analysis of trends and techniques in the fourth decade. J Card Surg 4(2): 113–124, 1989.

*Primary Examiner*—Jerome L. Kruter
*Attorney, Agent, or Firm*—Jon Carl Gealow; Keck, Mahin & Cate

[57] ABSTRACT

A tubular vascular graft made of synthetic or natural material. In one embodiment of this invention the effective lumen of the vascular graft is controlled by providing a fenestrated diaphragm within the tubular graft, the periphery of which diaphragm is in engagement with the inner wall of the tubular graft. The diaphragm is made weak on at least two radial lines extending from the inside surface of the tubular graft to the edge of the diaphragm's central orifice. The effective orifice of the tubular graft is that of the diaphragm's central orifice when the diaphragm is intact, but is enlarged to be that of the graft's lumen when the diaphragm is ruptured at its weak radial lines, such as by using a balloon dilatation catheter. In a second version the tubular graft has a second wall along a portion of its length. The second inner wall bulges inwardly from the inner surface of the tubular graft with a saline solution filling the space between the wall and forming the bulge. The bulge is ruptured and flattened against the inside wall of the graft by a balloon dilatation catheter.

12 Claims, 1 Drawing Sheet

FLOW CONTROL SYSTEMIC TO PULMONARY ARTERIAL SHUNT

BACKGROUND OF THE INVENTION

I. Field of the Invention

This invention relates to a vascular shunt connecting the systemic circulation to the pulmonary circulation as a treatment for children with cyanotic congenital heart diseases, the result of which is decreased pulmonary blood flow. More particularly it relates to a shunt which is most typically used as a palliative procedure to provide increased pulmonary blood flow until the child reaches the body weight deemed necessary for favorable surgical results from a complete "corrective" surgical procedure. As the child grows, increased blood flow through the shunt to the lungs, which have increased in size and mass, is desirable. In order to accommodate increased blood flow, a shunt path or paths are required, the flow area of which can be increased when desired.

II. Historical Background and Description of Related Art Including Information disclosed Under 37 CFR Secs. 1.97 & 1.98

The concept of a vascular shunt connecting the systemic circulation to the pulmonary circulation was first published by Drs. Blalock and Taussig in 1945. This was the first surgical procedure to treat children with cyanotic congenital heart diseases of the type which result in decreased pulmonary blood flow. This procedure continued as the only surgical option for children with cyanotic congenital heart disease until the 1950s when corrective surgical procedures were first attempted. Even though corrective surgical procedures are now regularly undertaken, systemic to pulmonary shunts continue to be a preferred treatment for children with complex cyanotic congenital heart disease. The shunts continue to be used as a palliative procedure which will allow the child to grow, thereby gaining body mass, prior to complete repair of the defective heart by corrective surgical procedures. The growth of the child normally assures better results from the corrective surgical procedures.

The systemic to pulmonary "Blalock-Taussig" or, as they are commonly known, "B-T" shunts, were originally performed by connecting a subclavian artery to a pulmonary artery in a side to end fashion, the so called "classic procedure". The "classic procedure" continued to be used until more than two decades later, when in the 1980s, synthetic material was first used to create a tubular structure for connecting a subclavian artery to a pulmonary artery in a side-by-side fashion. This so-called "modified procedure" is generally regarded as superior to the "classic procedure" since it preserves flow to the upper extremities through the subclavian artery and provides the ability to control the amount of blood flow to the lungs by choosing the size, i.e. the cross-sectional flow area or lumen of the shunt.

A review of developments with respect to the Blalock-Taussig shunt procedure is set forth in: *The Blalock-Taussig Shunt: An Analysis of Trends and Techniques in the Fourth Decade*, William L. Holman, M.D. et al, Journal of Cardiac Surgery, Vol. 4, No. 2, 1989, pages 113–124.

In many instances the volume of the pulmonary blood flow provided by the "modified procedure" B-T shunt becomes inadequate as the child grows, due to the limited blood volume which will pass through the fixed cross-sectional flow area or lumen of the B-T shunt. When this inadequacy develops, it has been found necessary to implant a second "modified procedure" B-T shunt, typically on the opposite subclavian artery from the first, so as to provide increased pulmonary blood flow until the child reached the body weight deemed desirable for favorable surgical results from a "corrective" surgical procedure.

Clearly, it would be highly desirable to avoid such a second procedure. It being desirable whenever possible to avoid a surgical procedure if the desired benefit to the patient can be provided without again opening the chest cavity. For instance, the necessity for a second through the chest wall invasive procedure could be eliminated if the previously implanted shunt could be dilated, that is increased in cross-sectional area, by a less traumatic procedure, such as by an angioplasty procedure, to accommodate the increased amount of pulmonary blood flow required by a growing child. The desirability of providing such a shunt is the genesis for this invention, which provides an expandable shunt for use in a "modified procedure" B-T shunt.

SUMMARY OF THE INVENTION

It is an object of this invention to provide an expandable or dilatable shunt for use in a "modified procedure" B-T shunt. It is a further object of this invention, in a preferred embodiment thereof, to provide an expandable or dilatable shunt which may be readily expanded or dilated by an angioplasty procedure. It is a still further object of this invention to provide an expandable or dilatable shunt having a predetermined cross-sectional flow area, which is formed with a portion of reduced cross-sectional flow area which when subjected to manipulation by an angioplasty procedure is rendered ineffective in reducing the predetermined cross-sectional flow area of the shunt.

In accordance with this invention, a tubular vascular graft is formed of synthetic or natural material. In a first preferred embodiment of this invention the effective lumen of the vascular graft is controlled by providing a fenestrated diaphragm, having an orifice at its center, within a tubular graft. The periphery of the diaphragm is secured to the inner surface of the tubular graft. The diaphragm is situated in the lumen of the tubular graft in a fashion very similar to that of a pulmonary or aortic valve in the pulmonary artery or aorta respectively, but located at the center of the graft's length rather than closer to one end. The diaphragm is made weak along two or more radial lines extending from the inside surface of the tubular graft to the edge of the diaphragm's orifice, similar to fused commissures of an aortic or pulmonary valves. Although, in the case of the aortic and pulmonary valves, the lines of commissures may not be the weakest points in the valve. The effective orifice, or cross-sectional flow area, of the tube is that of the diaphragm's orifice when the diaphragm is intact. The effective orifice can be enlarged to be that of the graft's lumen when the diaphragm is ruptured along its weak radial lines using a balloon dilatation catheter. The pieces of the diaphragm while detached from each other when the diaphragm is ruptured, remain firmly attached at their outer edge to the inside wall of the vascular graft.

In a second preferred embodiment of this invention, a portion of the length of the tubular graft is provided with an inner lining formed of a somewhat resilient or stretchable material. The two circumferential edges of the inner lining are securely sealed to the inner surface of the graft. An isotonic solution is captured between the inner lining and the inner surface of the graft. The graft being considerable less flexible than the inner lining, the saline solution causes the inner lining to stretch, forming inward bulge of the inner lining, thereby restricting the grafts lumen or cross-sectional flow area. The bulge may be ruptured and flattened against the inner surface of the graft by a balloon dilatation catheter, thereby increasing the cross-sectional flow area of the shunt to that of the tubular graft. The rupture of the inner lining results in the release of the saline solution into the blood stream.

DETAILED DESCRIPTION OF THE PREFERRED EMBODIMENTS

Figure 2:
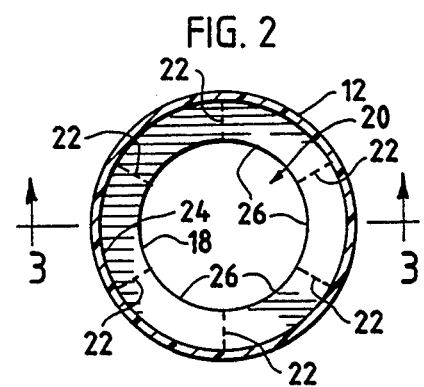
FIG. 2 is a cross-sectional view of a tube assembly in accordance with a first preferred embodiment of this invention.
Figure 1:
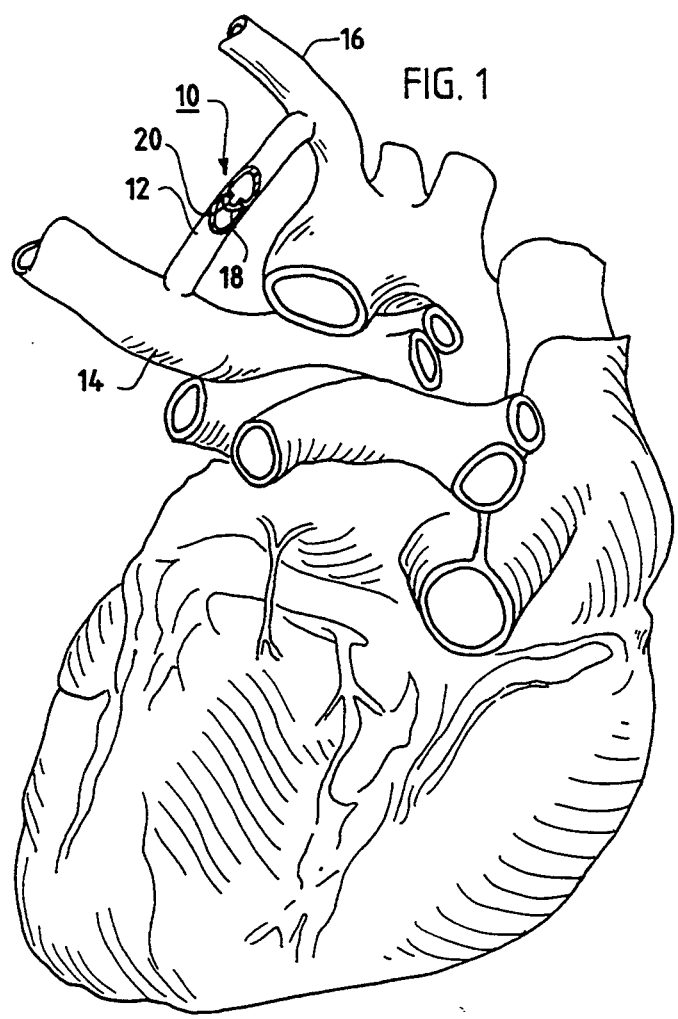
FIG. 1 is a perspective left lateral view of a heart with associated major veins and arteries showing a "modified procedure" B-T shunt placed between the left subclavian artery and the left pulmonary artery, using a tube assembly in accordance with this invention.
Figure 3:
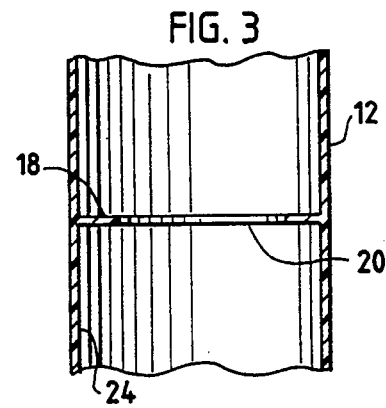
FIG. 3 is a cross-sectional view of the tube assembly of FIG. 2, taken along the line 3—3 in FIG. 2.

Referring to FIGS. 1–3 a shunt or graft in accordance with a first preferred embodiment of this invention will be described. The shunt or graft 10 includes a tubular structure 12 made from a synthetic material (e.g. polytetraflouroethylene or DACRON, a synthetic polyester textile fabric), or natural material (e.g. pericardium). The tubular structure 12 is implanted in a palliative surgical procedure connecting a systemic to a pulmonary artery. As shown in FIG. 1, the graft 10 is interposed between the left pulmonary artery 14 and the left subclavian artery 16.

The lumenal diameter of the tubular structure 12 is chosen to accommodate what would be considered sufficient blood flow to the lungs for the infant when it has grown and increased in body weight to that deemed desirable for favorable surgical results from a complete "corrective" surgical procedure. The lumen sizes would in most cases be in the range of 6 to 10 millimeters diameter. The choice of size in that range would depend on the neonate's or very young infants size or weight at the time of implant of the graft 10, and more particularly on the desired size or weight of the toddler when the corrective surgical procedure is to be undertaken.

As shown in FIGS. 1–3, the tubular structure 12 is provided with a fenestrated diaphragm 18 having a central orifice 20. When the graft 10 is implanted, blood flow is restricted to that which will pass through the central orifice 20. The diameter of the central orifice will in most cases be in the range of 4–5 millimeters. The choice of orifice size in that ranges depends on the neonate's or very young infant's size or weight at the time of implant of the graft 10. Blood flow through the graft 10 from the left subclavian artery to the left pulmonary artery and the lungs is restricted by the diaphragm 18 to properly accommodate a neonate's or a young infant's pulmonary blood flow.

The fenestrated diaphragm 18, as shown in FIG. 2 is provided with three to six weak areas 22, radially extending from the inner surface 24 of the tube 12 to closely adjacent the orifice 20 of the diaphragm 18. The weak areas 22 may be formed in the diaphragm 18 as it is manufactured, such as by weaving of thready material, or in a stamping or molding operation. As an alternative, the weak areas 22 may be formed in the diaphragm after it is manufactured, such as by scoring or the cutting of grooves. The number of weak areas 22 is not critical, being determined to some extent by the physical characteristics of the material forming the diaphragm, and by the manner in which the weak areas 22 are formed. The weak areas 22 are separated by an equal number of arcuate portions 26.

As the infant grows and his/her weight increases, observation of the child's physical condition will indicate when increased blood flow through the shunt 10 is desirable. For instance, when the aeration of the blood falls below normal levels, the body will assume a bluish hue, (cyanosis) due to the bluish color of non-aerated blood. When it is desired to increase the blood flow through the shunt 10, a balloon valvuloplasty catheter 28, is entered through the body wall (by arterial or venous access) and threaded through the arterial system to the left subclavian artery 16 and into the shunt 10. The deflated balloon 30 of the catheter is of a diameter which will pass through the orifice 20, such that the expansible balloon may be positioned in the orifice 20. The weak areas 22 serve as sites for rupture of the diaphragm 18 when the diaphragm's orifice is dilated by expansion of balloon 30 of balloon valvuloplasty catheter 28 as shown in FIG. 4.

Such dilation will result in enlarging the effective orifice or diameter of the shunt 10 to that of the tube 12, thereby increasing the blood flow to the lungs. Such a procedure is performed when the child outgrows the limited amount of pulmonary blood flow possible through the diaphragm's orifice. The increase in pulmonary blood flow achieved through enlarging the effective orifice will therefore eliminate the need for a second major surgical procedure to implant a second B-T shunt.

Figure 5:
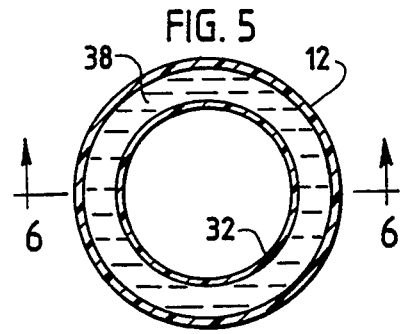
FIG. 5 is a cross-sectional view of a tube assembly in accordance with a second preferred embodiment of this invention.
Figures 4, 7:
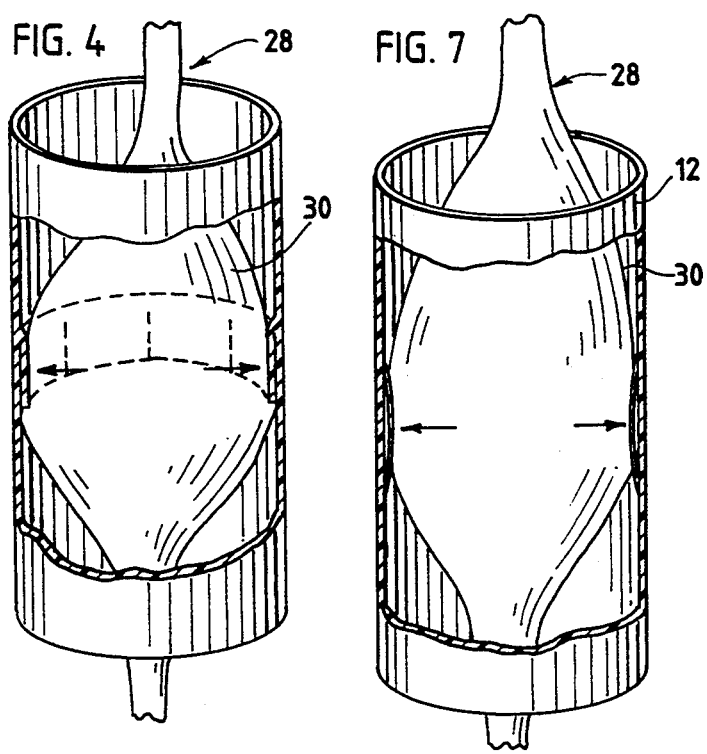
FIG. 4 is a perspective view of the tube assembly of FIG. 2, showing a balloon catheter expanded to rupture the diaphragm of the tube assembly.
FIG. 7 is a perspective view of the tube assembly of FIG. 5, showing a balloon catheter expanded to rupture the inner lining of the tube assembly.
Figure 6:
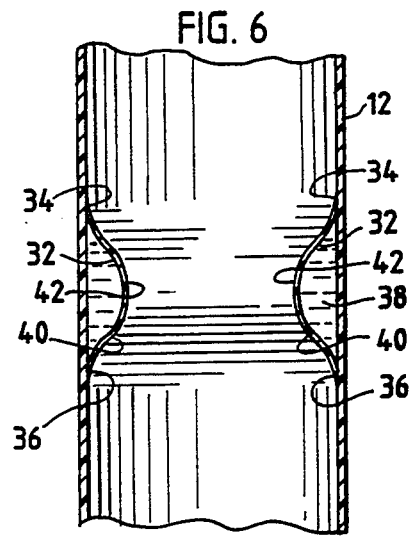
FIG. 6 is a cross-sectional view of the tube assembly of FIG. 5, taken along the line 6—6 in FIG. 5.

Referring to FIGS. 5–7 a shunt or graft in accordance with a second preferred embodiment of this invention will be described. As was the case with the first embodiment, the shunt or graft 10 includes a tubular structure 12 made from a synthetic material (e.g. polytetraflouroethylene or dacron), or natural material (e.g. pericardium). Again the tubular structure 12 is implanted in a palliative surgical procedure connecting a systemic to a pulmonary artery.

In the second embodiment of this invention, a central portion of the tubular graft 10, has a inner lining 32. The inner lining 32 is secured sealed to the inner surface of the tubular structure 12, along two circumferential edges 34 and 36. Prior to completely sealing one of the edges 34 or 36, an isotonic solution 38 is captured between the lining 32 and the inner surface of the graft 10. The graft 10 which forms the cylindrical outer shape of the tubular graft is relatively stiff, while the inner lining 32 is made of a stretchable material. The graft 10 being formed of a material considerable less flexible than lining 32, the isotonic solution 38 causes the lining 32 to stretch, forming inward bulge 40 of the inner lining, thereby restricting the grafts lumen or cross-sectional flow area.

The inwardly directed bulge 40 and its greatest thickness 42, restricts the lumen to a desired flow area which limits the amount of blood flow to the lungs when implanted surgically as a systemic to pulmonary artery shunt in a neonate. Yet more blood flow can be provided as the child grows by dilating and rupturing the lining 32 against the inner surface of graft 12 using a balloon dilatation catheter. Thus, the space between the inner surface of graft 10 and lining 32 forming the bulge 40 is filled with the isotonic solution 38, which will escape when the tubular lumen is dilated.

Much as described with respect to the first preferred embodiment of this invention, the bulge 40 may be ruptured and lining 32 flattened against the inner surface of the graft by a balloon dilatation catheter 28 as shown in FIG. 7, thereby increasing the cross-sectional flow area of the shunt to essentially that of the tubular graft. The rupture of the lining 32 by the expansion of balloon 30 results in the release of the small quantity of isotonic solution 38 into the blood stream, which is readily mixed and absorbed therein.

While in accordance with the U.S. Patent Statutes, preferred embodiments of the shunt of this invention have been shown and described, various changes may be made in the shunt and method of use of the shunt of this invention without parting from the true spirit and scope of this invention. The appended claims are intended to cover all such changes and modifications which fall within the true spirit and scope of this invention.

What is claimed is:

1. A tube assembly particularly adopted for use in a modified Blalock-Taussig shunt procedure providing fluid flow control comprising:
   an elongated tube of body compatible material, said tube having an inner wall surface which defines a first predetermined generally uniform fluid flow opening throughout its length, said tube having first and second ends, and
   a means secured to said inner wall surface of said tube and located along the length of said elongated tube between said first and second ends of said tube, providing a second predetermined restricted fluid flow opening which is smaller than said first predetermined flow opening, said first and second flow openings having a common central axis, said means when subjected to a predetermined force being altered such that it no longer provides said second predetermined flow opening, whereby the flow opening over the entire length of said tube is essentially said first predetermined flow opening.

2. The tube assembly of claim 1, wherein said tube is formed of a synthetic material.

3. The tube assembly of claim 1, wherein said synthetic material is reinforced expanded polytetrafluoroethylene.

4. The tube assembly of claim 1, wherein said tube is formed of a natural material.

5. The tube assembly of claim 1, wherein said tube is formed with an internal diameter in the range of 6 to 10 millimeters.

6. The tube assembly of claim 1, wherein said second predetermined flow opening has a diameter in the range of 4 to 5 millimeters.

7. A tube assembly particularly adopted for use in a modified Blalock-Taussig shunt procedure providing flow control comprising:
   a tube of body compatible material providing a first predetermined generally uniform internal flow opening, said tube having first and second ends, and
   a means located within said tube between said first and second ends of said tube providing a second predetermined flow opening, which second predetermined flow opening is smaller than said first predetermined flow opening, said means when subjected to a manipulative force being altered such that it no longer provides the second predetermined flow opening, whereby the flow opening over the entire length of said tube is said larger first predetermined flow opening.

8. A tube assembly particularly adopted for use in a modified Blalock-Taussig shunt procedure comprising:
   an elongated tube of body compatible material having a first predetermined generally uniform internal flow opening throughout its length, said tube having first and second ends, and
   a flow restriction means located within said tube, along the length of said elongated tube between said first and second ends of said tube, said flow restriction means providing a second predetermined flow opening which is smaller than said first predetermined flow opening, and a third predetermined flow opening which is essentially the same as said first predetermined flow opening, whereby said flow restriction means initially restricts the flow through said elongated tube to said second predetermined flow opening, and when said flow restriction means is subjected to a predetermined force, the flow opening through said tube is increased from said second predetermined flow opening to said third predetermined flow opening.

9. A modified Blalock-Taussig shunt procedure providing flow control comprising the steps of:
   A. implanting a shunt between the systemic circulation and the pulmonary circulation, said shunt including an elongated tube, said tube having an inner surface which defines a first predetermined generally uniform cross-sectional flow area throughout its length, said tube having first and second ends, and a means secured to said inner surface of said tube and located along the length of said elongated tube between said first and second ends of said tube, providing a second predetermined cross-sectional flow area which is smaller than said first predetermined cross-sectional flow area, said means when subjected to a predetermined force being altered such that it no longer provides said second predetermined cross-sectional flow area, whereby the cross-sectional flow area over the entire length of said tube is essentially said first predetermined cross-sectional flow area,
   B. threading a deflated balloon valvuloplasty catheter through the arterial system to the shunt so as to position the balloon within said second predetermined cross-sectional flow area in said means,
   C. expanding said balloon of said catheter to apply a force to said means, whereby said means is altered such that it no longer provides the second predetermined cross-sectional flow area, the cross-sectional flow area over the entire length of said tube being essentially said larger first predetermined cross-sectional flow area.

10. A tube assembly particularly adopted for use in a modified Blalock-Taussig shunt procedure providing flow control comprising:
- an elongated tube of body compatible material, said tube having an inner surface which defines a first predetermined generally uniform cross-sectional flow area throughout its length, said tube having first and second ends, and
- a diaphragm like member having an outer perimeter, said member secured around said outer perimeter to said inner surface of said tube and located along the length of said elongated tube between said first and second ends of said tube, said member having an orifice therein which provides a second predetermined cross-sectional flow area which is smaller than said first predetermined cross-sectional flow area, said member being provided with at least two radially extending weakened areas, such that when a physical force is applied to said member by positioning an instrument in said orifice which is expansible to occupy a cross-sectional area greater that said second predetermined cross-sectional flow area, said weakened areas will break, whereby the cross-sectional flow area through said tube will increase to essentially said first predetermined cross-sectional flow area.

11. A tube assembly particularly adopted for use in a modified Blalock-Taussig shunt procedure providing flow control comprising:
- an elongated tube of body compatible material, said tube having an inner surface which defines a first predetermined generally uniform cross-sectional flow area throughout its length, said tube having first and second ends, and
- a tubular lining located within said tube and extending over a portion of the axial length of said tube between said first and second ends of said tube, spaced circumferential edges of said lining being secured to said inner surface of said tube so as to form a closed volume between said inner surface of said tube and said lining, said volume being initially filled with a fluid, said lining providing a second predetermined cross-sectional flow area which is smaller than said first predetermined cross-sectional flow area, said liner being rupturable, when subjected to a predetermined force, to release said fluid, such that the cross-sectional flow area over the entire length of said tube will increase to essentially said first predetermined cross-sectional flow area.

12. The tube assembly of claim 4, wherein said fluid is a isotonic solution.

* * * * *

UNITED STATES PATENT AND TRADEMARK OFFICE
CERTIFICATE OF CORRECTION

PATENT NO. : 5,445,600
DATED : August 29, 1995
INVENTOR(S) : Ra-id Abdulla

It is certified that error appears in the above-indentified patent and that said Letters Patent is hereby corrected as shown below:

Column 8:

Claim 12, line 1, delete the numeral "4" and substitute the numeral - 11 -.

Signed and Sealed this

Fourteenth Day of November, 1995

*Attest:*

BRUCE LEHMAN

*Attesting Officer*     *Commissioner of Patents and Trademarks*